United States Patent
Kelman

(10) Patent No.: US 9,615,837 B2
(45) Date of Patent: Apr. 11, 2017

(54) SURGICAL TECHNIQUE AND INSTRUMENTATION FOR MINIMAL INCISION HIP ARTHROPLASTY SURGERY

(71) Applicant: Smith & Nephew, Inc., Memphis, TN (US)

(72) Inventor: David Clark Kelman, Somerville, TN (US)

(73) Assignee: Smith & Nephew, Inc., Memphis, TN (US)

(*) Notice: Subject to any disclaimer, the term of this patent is extended or adjusted under 35 U.S.C. 154(b) by 0 days.

(21) Appl. No.: 15/158,084

(22) Filed: May 18, 2016

(65) Prior Publication Data

US 2016/0256173 A1  Sep. 8, 2016

Related U.S. Application Data

(63) Continuation of application No. 15/049,915, filed on Feb. 22, 2016, which is a continuation of application
(Continued)

(51) Int. Cl.
*A61B 17/00* (2006.01)
*A61B 17/16* (2006.01)
(Continued)

(52) U.S. Cl.
CPC ...... *A61B 17/164* (2013.01); *A61B 17/00234* (2013.01); *A61B 17/1604* (2013.01);
(Continued)

(58) Field of Classification Search
None
See application file for complete search history.

(56) References Cited

U.S. PATENT DOCUMENTS 3,026,541 A   3/1962   Murat
3,029,811 A   4/1962   Yost
(Continued)

FOREIGN PATENT DOCUMENTS

AU    2004200392    7/2009
DE      2732325    1/1980
(Continued)

OTHER PUBLICATIONS

Multi-Reference 4-in-a Femoral Knee Instrumentation http://www.zimmer.com/ctl?op=global&action=1&ids=1065&template=MP printed on Oct. 13, 2004, 2 pages.
(Continued)

*Primary Examiner* — Sameh Boles
(74) *Attorney, Agent, or Firm* — Fish & Richardson P.C.

(57) ABSTRACT

Improved instruments for modifying a shape of a proximal femur of a patient for installation of a stem of a femoral component of a prosthetic hip during hip replacement surgery, comprising a handle including an elongated shaft extending downward approximately in a z-direction, a first offset extending from a bottom of the elongated shaft approximately in a y-direction, a second offset extending from the second offset approximately in an x-direction, and a shaping member elongated downward from the second offset approximately in the z-direction. Provided is an improved femoral broach and an improved osteotome. Also provided is a method of improving a patient's positioning during hip replacement surgery by using a variable configuration mattress for positioning the patient.

15 Claims, 12 Drawing Sheets

Related U.S. Application Data

No. 14/253,104, filed on Apr. 15, 2014, now Pat. No. 9,265,508, which is a continuation of application No. 13/019,635, filed on Feb. 2, 2011, now Pat. No. 8,734,451, which is a continuation of application No. 12/412,527, filed on Apr. 27, 2009, now Pat. No. 8,096,993, which is a continuation of application No. 10/991,641, filed on Nov. 18, 2004, now Pat. No. 7,591,821.

(60) Provisional application No. 60/520,970, filed on Nov. 18, 2003.

(51) Int. Cl.
*A61F 2/46* (2006.01)
*A61B 34/20* (2016.01)
*A61B 17/32* (2006.01)

(52) U.S. Cl.
CPC ...... *A61B 17/1659* (2013.01); *A61B 17/1668* (2013.01); *A61B 17/1675* (2013.01); *A61F 2/4607* (2013.01); *A61B 34/20* (2016.02); *A61B 2017/0046* (2013.01); *A61B 2017/320008* (2013.01); *A61F 2/4657* (2013.01); *A61F 2002/4623* (2013.01); *A61F 2002/4635* (2013.01)

(56) References Cited

U.S. PATENT DOCUMENTS

| | | | |
|---|---|---|---|
| 3,729,749 A | 5/1973 | Rosecrans |
| 3,815,599 A | 6/1974 | Deyerle |
| 3,955,568 A | 5/1976 | Neufeld |
| 4,207,633 A | 6/1980 | Smith et al. |
| 4,306,500 A | 12/1981 | Castanien et al. |
| 4,306,550 A | 12/1981 | Forte |
| D272,764 S | 2/1984 | Dohogne |
| 4,457,307 A | 7/1984 | Stillwell |
| 4,565,192 A | 1/1986 | Shapiro |
| 4,574,794 A | 3/1986 | Cooke et al. |
| 4,583,270 A | 4/1986 | Kenna |
| 4,587,964 A | 5/1986 | Walker et al. |
| 4,703,751 A | 11/1987 | Pohl |
| 4,765,328 A | 8/1988 | Keller et al. |
| 4,921,493 A | 5/1990 | Webb et al. |
| 4,938,762 A | 7/1990 | Wehrli |
| 4,952,213 A | 8/1990 | Bowman et al. |
| 4,977,629 A | 12/1990 | Jones |
| 4,990,149 A | 2/1991 | Fallin |
| 5,049,149 A | 9/1991 | Schmidt |
| 5,089,003 A | 2/1992 | Fallin et al. |
| 5,089,004 A | 2/1992 | Averill et al. |
| 5,129,909 A | 7/1992 | Sutherland |
| 5,190,549 A | 3/1993 | Miller et al. |
| 5,190,550 A | 3/1993 | Miller et al. |
| 5,261,915 A | 11/1993 | Durlacher et al. |
| 5,287,577 A | 2/1994 | Bremer et al. |
| 5,324,293 A | 6/1994 | Rehmann |
| 5,352,230 A | 10/1994 | Hood |
| 5,364,401 A | 11/1994 | Ferrante et al. |
| 5,443,471 A | 8/1995 | Swajger |
| 5,445,642 A | 8/1995 | McNulty et al. |
| 5,486,178 A | 1/1996 | Hodge |
| 5,531,750 A | 7/1996 | Even-Esh |
| 5,569,260 A | 10/1996 | Petersen |
| 5,581,892 A | 12/1996 | Dean |
| 5,607,431 A | 3/1997 | Dudasik et al. |
| 5,676,668 A | 10/1997 | McCue et al. |
| 5,681,315 A | 10/1997 | Szabo |
| 5,683,395 A | 11/1997 | Mikhail |
| 5,683,397 A | 11/1997 | Vendrely et al. |
| 5,688,279 A | 11/1997 | McNulty et al. |
| 5,693,056 A | 12/1997 | Carls et al. |
| 5,704,941 A | 1/1998 | Jacober et al. |
| 5,709,689 A | 1/1998 | Ferrante et al. |
| 5,810,827 A | 9/1998 | Haines et al. |
| 5,810,830 A | 9/1998 | Noble et al. |
| 5,897,559 A | 4/1999 | Masini |
| 5,919,195 A | 7/1999 | Wilson et al. |
| 5,935,128 A | 8/1999 | Carter et al. |
| 5,938,665 A | 8/1999 | Martin |
| 5,993,455 A | 11/1999 | Noble |
| D433,506 S | 11/2000 | Asfora |
| 6,187,006 B1 | 2/2001 | Keller |
| 6,224,605 B1 | 5/2001 | Anderson et al. |
| 6,258,095 B1 | 7/2001 | Lombardo et al. |
| 6,273,915 B1 | 8/2001 | Grimes |
| 6,327,724 B1 | 12/2001 | Sharrock et al. |
| D454,952 S | 3/2002 | Ku et al. |
| D455,212 S | 4/2002 | Albrektsson et al. |
| 6,409,768 B1 | 6/2002 | Tepic et al. |
| 6,554,837 B1 | 4/2003 | Hauri et al. |
| 6,558,391 B2 | 5/2003 | Axelson et al. |
| 6,595,997 B2 | 7/2003 | Axelson et al. |
| 6,626,913 B1 | 9/2003 | McKinnon et al. |
| 6,676,706 B1 | 1/2004 | Mears et al. |
| 6,685,711 B2 | 2/2004 | Axelson et al. |
| 6,692,503 B2 | 2/2004 | Foley et al. |
| 6,695,850 B2 | 2/2004 | Diaz |
| 7,105,028 B2 | 9/2006 | Murphy |
| 7,396,357 B2 | 7/2008 | Tornier et al. |
| D598,096 S | 8/2009 | Petersen |
| D599,479 S | 9/2009 | Petersen |
| D600,346 S | 9/2009 | Petersen |
| 7,591,821 B2 | 9/2009 | Kelman |
| D648,850 S | 11/2011 | Kelman |
| 8,096,993 B2 | 1/2012 | Kelman |
| 2002/0099446 A1 | 7/2002 | MacArthur |
| 2002/0198531 A1 | 12/2002 | Millard et al. |
| 2003/0050645 A1 | 3/2003 | Parker et al. |
| 2003/0069591 A1 | 4/2003 | Carson et al. |
| 2003/0187449 A1 | 10/2003 | McCleary et al. |
| 2003/0220698 A1 | 11/2003 | Mears et al. |
| 2004/0010261 A1 | 1/2004 | Hoag et al. |
| 2004/0127887 A1 | 7/2004 | Zinkel |
| 2004/0153062 A1 | 8/2004 | McGinley et al. |
| 2004/0153191 A1 | 8/2004 | Grimm et al. |
| 2005/0048853 A1 | 3/2005 | Pacha |
| 2005/0107801 A1 | 5/2005 | Davies et al. |
| 2005/0171548 A1 | 8/2005 | Kelman |
| 2005/0181548 A1 | 8/2005 | Yanagisawa et al. |
| 2005/0216022 A1 | 9/2005 | Lechot et al. |
| 2005/0234462 A1 | 10/2005 | Hershberger et al. |
| 2005/0234463 A1 | 10/2005 | Hershberger et al. |
| 2007/0093897 A1 | 4/2007 | Gerbec et al. |
| 2007/0233134 A1 | 10/2007 | Bastian et al. |
| 2007/0293871 A1 | 12/2007 | Ackermann |
| 2007/0299451 A1 | 12/2007 | Tulkis |
| 2008/0033444 A1 | 2/2008 | Bastian et al. |
| 2008/0255565 A1 | 10/2008 | Fletcher |
| 2009/0275948 A1 | 11/2009 | Kelman |
| 2010/0121331 A1 | 5/2010 | Sharp et al. |
| 2011/0247633 A1 | 10/2011 | Kelman |
| 2011/0295259 A1 | 12/2011 | Kelman |

FOREIGN PATENT DOCUMENTS

| | | |
|---|---|---|
| DE | 19850980 | 11/2000 |
| DE | 202008017200 | 4/2009 |
| EP | 359097 | 3/1990 |
| EP | 415837 | 3/1991 |
| EP | 380451 | 4/1991 |
| EP | 619097 | 10/1994 |
| EP | 645127 | 3/1995 |
| EP | 1566147 | 8/2005 |
| FR | 2742334 | 5/1998 |
| FR | 2796261 | 1/2001 |
| FR | 2854786 | 11/2004 |
| JP | 4044759 | 2/1992 |
| WO | WO0051530 | 9/2000 |
| WO | WO03026517 | 4/2003 |

(56) References Cited

FOREIGN PATENT DOCUMENTS

| WO | WO03065906 | 11/2003 |
|----|------------|---------|
| WO | WO03092513 | 11/2003 |
| WO | WO2004024007 | 3/2004 |

OTHER PUBLICATIONS

HSS/HSS.Newsroom: New Knee Replacement Reduces Recovery Time http://www/hss/edu/Newsroom/New/Knee/Replacement/Reduces/Recover/Time, printed on Mar. 5, 2003, 2 pages.

Mobile Bearing Knee, Genesis II and Profix, Acufex EndoButton CL, Brochure, 3 pages, undated.

Posterior Reference NexGen System Complete Knee Solution, Multi/Reference™ r/in/1 Femoral Instrumentaton, Posterior Reference Surgical Technique for NexGen Cruciate Retaining & Legacy® Posterior Stabilized Knees, Zimmer brochure, pp. 1/16, 1996.

Xcelerate™ 4/in/1 Ceramic Cutting Blocks Extremely Accurate Cutting with the Potential for Reduced Intraoperative Wear Debris, Stryker Howmedica Osteonics brochure, 2 pages, undated.

BioRCI/HA Bioabsorbable Screws with Hydroxylapatite, The Innovative Choice for Exceptional Strength and Selection, Smith & Nephew brochure, pp. 3/10, undated.

Matrix Opti/Fix Plus, Surgical Technique Developed in Conjunction with John M. Cuckler, M.D., University of Alabama, Birmingham, Alabama, Smith & Nephew brochure, pp. 1/36, Dec. 1996.

Miller, Steve, "Echelon Instrumentation Options," OrthoUpdate, Smith+Nephew, 2 pages, undated.

Surgical Technique, Innovations in Minimally Invasive Joint Surgery, Minimally Invasive Hip Replacement Through the Posterior Approach, Smith & Nephew brochure, 20 pages, Oct. 2003.

Paralign Hip Instrument MIS Systems, Orthogroup, 4 pages, undated.

Deirmengian, et al, "A Technique for the Minimally Invasive, Watson-Jones Approach to Total Hip Arthroplasty," Operative Techniques in Orthopaedics, 2006, pp. 126-134.

Nogler, et al, "A Double Offset Broach Handle for Preparation of the Femoral Cavity in Minimally Invasive Direct Anterior Total Hip Arthroplasty," The Journal of Arthroplasty, vol. 21, No. 8, 2006, pp. 1206-1208.

International Preliminary Report on Patentability for International Application No. PCT/US2010/057326, mailed May 22, 2012.

Office Action for U.S. Appl. No. 12/623,030, mailed Jul. 25, 2012.

Office Action for U.S. Appl. No. 13/019,635, mailed Oct. 16, 2012.

Office Action for U.S. Appl. No. 13/019,635, mailed Jun. 6, 2013.

Patent Examination Report No. 2 for Australian Application No. 2011244995, mailed Sep. 8, 2014.

Supplementary Partial European Search Report for European Application EP 10 83 2220, issued Mar. 27, 2015.

SURGICAL TECHNIQUE AND INSTRUMENTATION FOR MINIMAL INCISION HIP ARTHROPLASTY SURGERY

CROSS-REFERENCE TO RELATED APPLICATIONS

The present application is a continuation of U.S. patent application Ser. No. 15/049,915, filed Feb. 22, 2016, which is a continuation of U.S. patent application Ser. No. 14/253, 104, filed Apr. 15, 2014, now allowed, which is a continuation of U.S. patent application Ser. No. 13/019,635, filed Feb. 2, 2011, entitled "Surgical Technique and Instrumentation for Minimal Hip Arthroplasty Surgery", now U.S. Pat. No. 8,734,451, which is a continuation of U.S. patent application Ser. No. 12/412,527, filed Apr. 27, 2009, entitled "Surgical Technique and Instrumentation for Minimal Incision Hip Arthroplasty Surgery," now U.S. Pat. No. 8,096, 993, which is a continuation of Ser. No. 10/991,641, filed Nov. 18, 2004, entitled "Surgical Technique and Instrumentation for Minimal Incision Hip Arthroplasty Surgery," now U.S. Pat. No. 7,591,821, which claims the benefit of U.S. Provisional Patent Application No. 60/520,970 filed Nov. 18, 2003, the entire contents of all of which are herein incorporated by reference.

FIELD OF THE INVENTION

The present invention relates to methods and instruments used for minimal incision surgery, and, more particularly, to method and instruments used to prepare a patient's femur prior to the implantation of a hip prosthesis' femoral component during hip replacement.

BACKGROUND

Joint implants, also referred to as joint prostheses, joint prosthetic implants, joint replacements, or prosthetic joints, are long-term surgically implantable devices that are used to partially or totally replace diseased or damaged joints, such as a hip, a knee, a shoulder, an ankle, or an elbow, within the musculoskeletal system of a human or an animal. Since their first introduction into clinical practice in the 1960s, joint implants have improved the quality of life of many patients. Both artificial hip joints and artificial shoulder joints are generally ball and socket joints, designed to match as closely as possible the function of the natural joint. Generally, the artificial socket is implanted in one bone, and the artificial ball articulates in the socket. A stem structure attached to the ball is implanted in another of the patient's bones, securing the ball in position.

The ball and socket joint of the human hip unites the femur to the pelvis, wherein the bali-shaped head of the femur is positioned within a socket-shaped acetabulum of the pelvis. The head of the femur or ball fits into the acetabulum, forming a joint which allows the leg to move forward, backward, and sideways in a wide range. The acetabulum is lined with cartilage, which cushions the bones and allows the joint to rotate smoothly and with minimal friction. An envelope of tough ligaments connects the pelvis and femur, covering the joint and stabilizing it. Cartilage also makes the joint strong enough to support the weight of the upper body and resilient enough to absorb the impact of exercise and activity. A healthy hip allows the leg to move freely within its range of motion while supporting the upper body and absorbing the impact that accompanies certain activities.

Various degenerative diseases and injuries may necessitate replacement of all or a portion of a hip using synthetic materials. Prosthetic components are generally made from metals, ceramics, or plastics, or combinations of them.

Total hip arthroplasty and hemi-arthroplasty are two procedures well known within the medical profession for replacing all or part of a patient's hip. These procedures have enabled hundreds of thousands of people to live fuller, more active lives. A total hip arthroplasty replaces both the femoral component and the acetabular surface of the joint, and so both a femoral prosthesis and an acetabular prosthesis are required. A hemi-arthroplasty may replace either the femoral component or the acetabular surface of the joint. The purpose of hip replacement surgery is to remove the damaged and worn parts of the hip and replace them with artificial parts, called prostheses, with the purpose of at least partially restoring the hip's function, including but not limited to, restoring the stability, strength, range of motion, and flexibility of the joint.

In total hip replacement surgery, commonly referred to as total hip arthroplasty, a patient's natural hip is replaced by two main components: an acetabular cup component that replaces the acetabular socket, and the femoral component, or the stem-and-ball component, that replaces the femoral head.

A conventional acetabular cup component may include a cup, a cup and a liner, or in some cases only a liner, all of which may be formed in various shapes and sizes. Generally, a metal cup and a polymeric liner are used. However, the liner may be made of a variety of materials, including polyethylene, ultra high molecular weight polyethylene, and ceramic materials. The cup is usually of generally hemispherical shape and features an outer, convex surface and an inner, concave surface that is adapted to receive a cup liner. The liner fits inside the cup and has a convex and concave surface. The cup liner is the bearing element in the acetabular component assembly. The convex surface of the liner corresponds to the inner concave surface of the cup or acetabulum, and the liner concave surface receives the head of a femoral component. An acetabular cup may include a highly polished inner surface to decrease wear.

The femoral or stem-and-ball component of the hip prosthesis generally includes a spherical or near-spherical head attached to an elongate stem, with a neck connecting the head and stem. In use, the elongate stem is located in the intramedullary canal of the femur, and the spherical or near-spherical head articulates relative to the acetabular component. Femoral prostheses used in total hip arthroplasty procedures may or may not differ from an endoprosthesis used in a hemi-arthroplasty. The femoral head of each type prosthesis is generally a standard size and shape. Various cups, liners, shells, stems and other components may be provided in each type arthroplasty to form modular prostheses to restore function of the hip joint.

During a total hip replacement, the surgeon will take a number of measurements to ensure proper prosthesis selection, limb length, and hip rotation. After making the incision, the surgeon works between the large hip muscles to gain access to the joint. The femur is pushed out of the socket, exposing the joint cavity. The deteriorated femoral head is removed.

In order to install the acetabular cup, the surgeon prepares the bone by reaming the acetabular socket to create a surface for accepting a cup. The cup may be held in place by bone cement or an interference or press fit, or it may have a porous outer surface suitable for bony ingrowth. The new acetabular shell is implanted securely within the prepared hemispherical socket. The plastic inner portion of the implant is placed within the metal shell and fixed into place.

Next, the femur is prepared to receive the stem. The proximal end of the femur is at least partially resected to expose the central portion of the bone. Generally, at least part of the greater femoral trochanter is resected to gain access to the central portion of the femur, specifically, the medullary canal. In the central portion, a cavity is created that matches the shape of the implant stem, utilizing the existing medullary canal. The top end of the femur is planed and smoothed so that the stem can be inserted flush with the bone surface. If the ball is a separate piece, the proper size is selected and attached. Finally, the ball is seated within the cup so that the joint is properly aligned, and the incision is closed.

During shoulder replacement, the ball and socket joint of the human shoulder is replaced with a prosthetic joint using a procedure similar to that described above. During a shoulder replacement operation, at least a portion of the proximal section of the humeral shaft is replaced by a metal prosthesis. This prosthesis generally consists of two parts: a stem that is mounted into the medullary canal of the humerus, and a head component connected in some manner to the stem. The head component replaces the bearing surface of the humerus and articulates within the glenoid cavity of the scapula to allow movement of the shoulder.

An arthritic humeral head (ball of the joint) may be removed and replaced with a humeral prosthesis. If the glenoid socket is unaffected, a hemiarthroplasty may be performed (which means that only the ball is replaced). The humeral component is made of metal and is usually press fit, but sometimes cemented, into the shaft of the bone of the humerus.

If the glenoid is affected, but conditions do not favor the insertion of a glenoid component, a non-prosthetic glenoid arthroplasty may be performed along with a humeral hemi-arthroplasty. In this procedure, the humeral prosthesis is installed, and the patient's glenoid shape and orientation are corrected to articulate the humeral prosthesis, for example, by reshaping the socket by reaming. The prosthetic ball of the humeral component then articulates with the reshaped bony socket of the glenoid. In a total shoulder joint replacement, or total humeral arthroplasty, the glenoid bone is shaped by reaming and oriented, and then covered with a prosthetic glenoid component that is commonly stabilized by bone cement.

During joint replacement surgery, such as the procedures described above, a rather large incision is typically required to allow the surgeon adequate access to the joint. The large incision is needed to properly use the instruments needed to prepare the bones for installation of the prosthetic joint components and to install the prosthesis itself. For example, during total hip replacement surgery, some conventional surgical techniques generally require an approximately 25 to 35 cm incision in the lateral (side) or posterior (back) aspect of the patient for installing, respectively, the acetabular component and the femoral component of the prosthetic hip. Other conventional surgical techniques include two smaller incisions: a first, anterior incision to install the acetabular member; and the second, posterior incision to install the femoral component. In this technique, both the first and the second incisions are approximately 3 cm to approximately 5 cm in length. The two-incision technique is considered advantageous over the one incision technique because it minimizes the trauma to the patient and results in quicker and better patient rehabilitation than the technique involving a longer incision. Currently available data suggests that the longer incision, either posterior or lateral, increases patient morbidity. Thus, for joint replacement surgery, particularly for hip replacement surgery, it is desirable to reduce the size and the number of the incisions without jeopardizing surgical access to the joint.

Patient positioning during hip arthroplasty is important for surgical access, proper preparation of the joint, and installation of the prosthetic components. Both initial positioning of the patient for the surgery and maintenance of the patient's position throughout the surgery are essential. Various approaches to improving patient positioning exist. For example, some of the conventional hip arthroplasty techniques use supine (on the back) positioning of the patient, with an operating or surgical table including a dropping part on one side of the lower end. This allows the lowering of the patient's operative leg for increased access to the proximal femur.

During recent years, an effort has been made to reduce the size of the incision needed to implant joint prostheses through so-called "minimally invasive" surgery ("MIS"). The term "minimally invasive surgery" generally refers to the surgical techniques that minimize the size of the surgical incision and trauma to tissues, and are generally less intrusive than conventional surgery, thereby shortening both surgical time and recovery time. Minimally invasive arthroplasty techniques are advantageous over conventional arthroplasty techniques by providing, for example, a smaller incision, less soft-tissue exposure, improved ligament balancing, and minimal trauma to the muscle and ligament mechanisms. To achieve the above goals of MIS, it is necessary to modify traditional implants, instruments, and surgical techniques to decrease the length and number of the surgical cuts, as well as to decrease the exposure of and trauma to the internal joint structures. The benefits of MIS surgery can be significant, at least partially because smaller and fewer incisions and the less intrusive nature of the procedure shorten both surgical time and recovery time. Thus, it is advantageous to modify traditional implants, instruments, and methods to make them particularly suitable for use in minimally invasive surgical procedures.

Another recent development in joint replacement is computer-assisted or computer-aided surgical (CAS) systems that use various imaging and tracking devices and combine the image information with computer algorithms to track the position of the patient's leg, the implant, and the surgical instruments and to make highly individualized recommendations on the most optimal surgical cuts and prosthetic component selection and positioning. Several providers have developed and are marketing imaging systems based on CT scans and/or MRI data or on digitized points on the anatomy. Other systems align preoperative CT scans, MRIs, or other images with intraoperative patient positions. A preoperative planning system allows the surgeon to select reference points and to determine the final implant position. Intraoperatively, the system calibrates the patient position to that preoperative plan, such as by using a "point cloud" technique, and can use a robot to perform surgical procedures. Other systems use position and/or orientation tracking sensors, such as infrared sensors acting stereoscopically or otherwise, to track positions of body parts, surgery-related items such as implements, instrumentation, trial prosthetics, prosthetic components, and virtual constructs or references such as rotational axes that have been calculated and stored based on designation of bone landmarks. Processing capability such as any desired form of computer functionality, whether standalone, networked, or otherwise, takes into account the position and orientation information as to various items in the position sensing field (which may correspond generally or specifically to all, portions, or more than all of the surgical field) based on sensed position and orientation of their associated fiducials or based on stored position and/or orientation information. The processing functionality correlates this position and orientation information for each object with stored information regarding the items, such as a computerized fluoroscopic imaged file of a bone, a wire frame data file for rendering a representation of an instrumentation component, a trial prosthesis or actual prosthesis, or a computer generated file relating to a rotational axis or other virtual construct or reference. The processing functionality then displays position and orientation of these objects on a screen or monitor or otherwise. The surgeon may navigate tools, instrumentation, trial prostheses, actual prostheses and other items relative to bones and other body parts in order to perform joint replacement more accurately, efficiently, and with better alignment and stability. Instruments and surgical techniques that can be used in computer-assisted surgery are highly desirable.

It is highly desirable to adapt the surgical instruments used in preparation of the femoral bone during hip replacement to minimally invasive surgery, computer assisted surgery, or both. The instruments used in femoral preparation include, but are not limited to, osteotomes or chisels used for resecting at least a portion of the femoral head to expose the central portion of the femur, and broaches, reamers, and rasps, used to clean and enlarge the hollow center of the bone, creating a cavity that matches the shape of the femoral component's stem.

During hip replacement surgery, the surgeon opens a femoral intramedullary canal by removing a portion of the trochanteric fossa with an osteotome or a chisel, an instrument for surgical division or sectioning of bone. The surgeon then uses one or a series of increasing size cavity preparation devices, such as reamers or broaches, to prepare a cavity for installation of a femoral stem. By using a series of gradually increasing in size devices, the surgeon expands the intrafemoral cavity until the desired size and shape is created. Sometimes, the portion of the final broach inserted into the femoral cavity serves as a trial femoral stem.

For the success of hip replacement, it is generally desired to select and install the femoral stem of the largest size suitable for a particular patient. Electing the largest appropriate femoral stem helps to stabilize the femoral component in the femur, improves alignment, and reduces the potential of the femoral component's loosening and failure. There is a need for instruments and method for preparation of a femoral cavity that permit installation of an appropriately sized stem of the femoral component in order to improve alignment and stabilization of the femoral component in the patient with minimum interference the tissue of the patient In minimally invasive surgery, the need to insert and operate the femoral preparation instruments through smaller incisions may conflict with the proper instrument alignment needed to create the cavity of the largest possible size. For proper access and alignment, long incisions and other invasive procedures are often required. The single-incision lateral or posterior approach hip-arthroplasty procedure may simplify access to the femur, but it requires muscle dissection. The two-incision procedures, on the other hand, make approach to the femur difficult. When the anterior approach to the femur is used, muscle dissection is not necessary, but properly positioning the femur to allow access along the long axis often requires releasing the posterior hip capsule. The posterior capsule comprises a blood vessel, and surgically releasing the capsule greatly releases the risk of bleeding. The anterior approach used with some traditional instruments, such as straight femoral reamers, results in extensive trauma to the patient's tissues. Therefore, there is an unrealized need for instruments and techniques for preparation of a femoral cavity that reduce the incision size and trauma to tissues without jeopardizing preparation of the cavity of the largest appropriate size, which provide for proper sizing and alignment of the femoral component's stem, and which will improve restoration of hip function and reduce the risk of the prosthesis loosening and failing.

In summary, there is a current unrealized need for improved devices, systems and procedures adapted for use in minimally invasive surgery (MIS). There is a particular unrealized need for improved devices for preparation of a patient's femur for installing a femoral component of a hip prosthesis. Improved devices are desired that are adapted for introduction and operation through a smaller surgical incision than conventionally available devices. Also needed are improved devices, systems, and procedures that would minimize the damage to the flesh, muscle, and other soft tissues during insertion, operation, and withdrawal. At the same time, there is a need for improved devices, systems, and procedures that would improve sizing and aligning of the femoral components and reduce the risk of their loosening. Also desired are improved devices, systems, and procedures suitable for computer-assisted surgery.

In general, devices and systems are needed that are easy to use and manufacture, minimize tissue damage, simplify surgical procedures, are versatile, allow for faster healing with fewer complications, require less post-surgical immobilization, and are less costly to produce and operate.

SUMMARY

According to various aspects and embodiments of the present invention, there are provided devices, systems, instruments and methods for preparation of a femur for installing a femoral component of a hip prosthesis. More specifically, certain aspects and embodiments of the present invention provide systems for modifying the shape, or shaping, of a proximal femur of a patient for installation of a stem of the femoral component during total or partial hip replacement surgery. Modifying the shape of a proximal femur includes, but is not limited to, resection of bone or other tissues, preparation of a femoral cavity for receiving the stem of the femoral component, or both.

Improved instruments for modifying the shape of a proximal femur of a patient for installation of a stem of a femoral component of a prosthetic hip during hip replacement surgery, comprise a handle including an elongated shaft extending downward approximately in a z-direction, a first offset extending from a bottom of the elongated shaft approximately in a y-direction, a second offset extending from the second offset approximately in an x-direction, and a shaping member elongated downward from the second offset approximately in the z-direction. When the patient is in a supine position during surgery, during and upon installation of the instruments, the offsets locate the handle in a general medial-lateral direction away from the shaping member and vertically out of the surgical wound. The offsets allow installation of the instrument into the hip joint through an incision that is smaller than required for installation of the conventional instruments, and minimizes or eliminates the need to resect the posterior capsule. The improved systems also eliminate the need to deliver the femur out of the surgical wound for preparation.

The devices, systems, instruments and methods according to aspects and embodiments of the present invention are especially well suited for use in minimally invasive hip arthroplasty. The devices can be used in conjunction with image guided navigational systems, computer-assisted systems, or other systems for precision guiding. The devices, systems and instruments can further comprise fiducials for permitting the tracking of the position and orientation of the instruments or devices by the position sensors. The devices, systems, instruments and methods according to certain aspects and embodiments of the present invention are not limited to use in minimally invasive surgery or computer-assisted surgery but can also be adapted for use in conventional hip arthroplasty or other surgical procedures.

The disclosed embodiments of the present invention provide femoral preparation devices, instruments, and systems comprising such devices and instruments, that allow installation and use through a minimally invasive surgical incision. According to aspects and embodiments of the present invention, the instruments for preparation of the femur include, but are not limited to, osteotomes, chisels, broaches, reamers or rasps. The instruments typically comprise shaping members, which may further comprise cutting elements such as teeth or sharp edges, or other elements for shaping of bone tissue and/or other tissues. The shaping member is typically at least partially inserted into the hip joint during surgery. In an instrument for preparation of a femoral cavity, such as a broach, the shaping member is typically at least partially inserted into the femur, more specifically, into the intramedullary canal of the femur.

The devices and instruments according to the aspects and embodiments of the present invention can include, be connected to, or used in conjunction with heads, handles, drills, mallets, or other implements for directing and manipulating the devices. The devices and instruments can comprise cannulated or hollow structures. The devices and instruments can also include one or more shafts connecting various elements. The devices, instruments, or systems can be one-piece or multi-piece, or modular. In modular devices, instruments and systems, elements of the devices can be connected and used in various combinations, thereby increasing the system's versatility. Additionally, the instruments, devices, and systems of the present invention can incorporate elements of variable shape, such as flexible elements.

During use, the femoral preparation devices are rotated or moved either by hand or operated with a power tool, so that the cutting implements shape bone, cartilage, marrow, and other tissues. In some cases, the devices are adapted to remove the tissue in small pieces. The resected tissue may pass through or be contained within the central cavity of the device, may pass outside the device, or may be removed by appropriate implements.

The uses of the devices and instruments according to embodiments of the present invention are not limited to hip arthroplasty. They may also be used in connection with various other situations where resecting bone, creating a central cavity in a bone, or both, is desirable. Particularly, the devices and instruments according to aspects and embodiments of the present invention can be adapted to a range of joint arthroplasties.

In one embodiment, the osteotome systems are provided for resecting at least a portion of the patient's femoral head, particularly at least a portion of the greater trochanter prominence, when preparing the femur for installation of a hip prosthesis' femoral component. In a proffered embodiment a box osteotome comprising an approximately box-shaped cutting section with an open distal end is used to remove an approximately box-shaped portion of a patient's femoral head and to open a femoral canal. In another embodiment broach systems are provided for preparation of a requisite femoral cavity in a patient's femur adapted for installation of the stem of the femoral component of a hip prosthesis.

In one embodiment, the systems and methods of the present invention allow the surgeon to advantageously realize the anterior approach to the femoral head during hip replacement surgery without releasing the posterior hip capsule, thereby decreasing trauma to the patient and risk of bleeding. By allowing the surgeon to advantageously use an improved anterior approach, rather than a posterior or a lateral approach that require extensive muscle dissection, the systems and methods of the present invention improve the hip arthroplasty patient's recovery. The systems and methods of the present invention can be advantageously used with a variety of prosthetic hip systems, including, but not limited to the conventional systems, such as those employing a Mueller femoral stem that traditionally requires a posterior/lateral approach for installation.

The instruments and systems according to aspects and embodiments of the present invention can be made of a variety of materials suitable for surgical instruments, including but not limited to metals, plastics, polymers, glass, ceramics, composite materials, or any combination or variation of those. Methods of using the improved instruments for preparation of a hip joint for installation of a prosthetic hip, particularly for preparation of a femur for installation of the prosthetic hip's femoral component, are also provided.

According to some aspects, the embodiments of the present invention provide hip arthroplasty systems and methods that improve patient positioning during hip replacement surgery, thereby simplifying access to the femur. In one embodiment, improved patient positioning is achieved by employing a mattress of variable configuration that allows positioning of a patient's leg for better access during hip arthroplasty.

In certain aspects and embodiments, the instruments, systems, and methods of the present invention minimize the size, the number, or both of the surgical incisions required for installation of a hip prosthesis and trauma to patient's tissues resulting from the surgery. In one aspect, the embodiments of the present invention are directed at minimizing the surgical incision and tissue trauma resulting from installation of a femoral component of a prosthetic hip joint.

The systems and methods according to some aspects and embodiments of the present invention allow installation of a hip prosthesis using one surgical incision, preferably an anterior incision. One advantage of using a single, preferably anterior, incision, is that it avoids the dissection of muscles during the surgical approach, resulting in less trauma to the patient, quicker recovery, and quicker return to normal daily activity In yet one more aspect, the embodiments of the present invention provide a method for improving patient positioning during hip arthroplasty. The improved method allows better access to the hip joint, particularly to the femur, and permits quick and simple modification of the conventional surgical systems used in hip arthroplasty to improve patient positioning.

It is to be understood that principles and concepts of the aspects and embodiments of the present invention are not limited to structures, methods, and applications provided herein but can be applied to any suitable surgical application or device. Modifications and combinations of the foregoing aspects of the present invention are envisioned and fall within its scope.

The foregoing discloses preferred embodiments of the present invention, and numerous modifications or alterations may be made without departing from the spirit and the scope of the invention.

The drawings illustrating preferred embodiments of the present invention, are schematic representation. The actual systems, devices and methods according to the preferred embodiments of the present invention may depart from the foregoing schematics.

PREFERRED EMBODIMENTS

Femoral Broach

Figure 1:
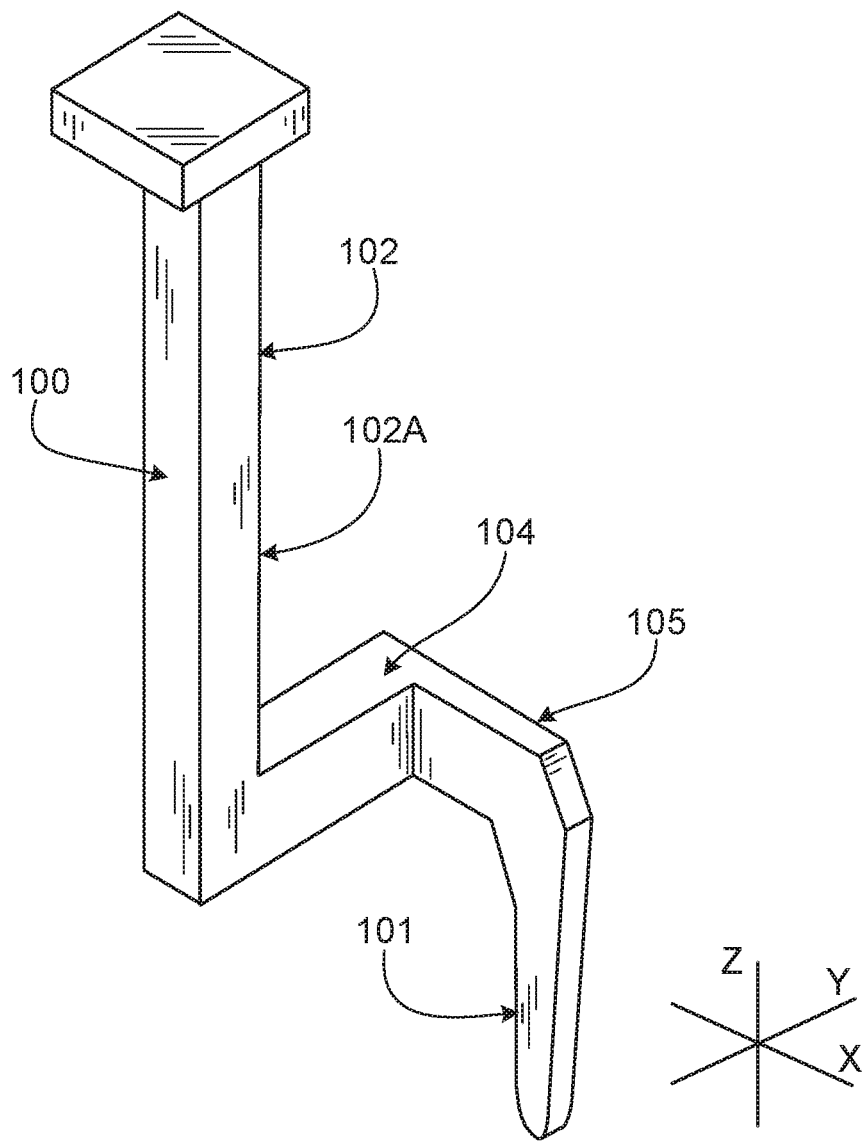
FIG. 1 is a schematic isometric view of an improved femoral broach.
Figure 2:
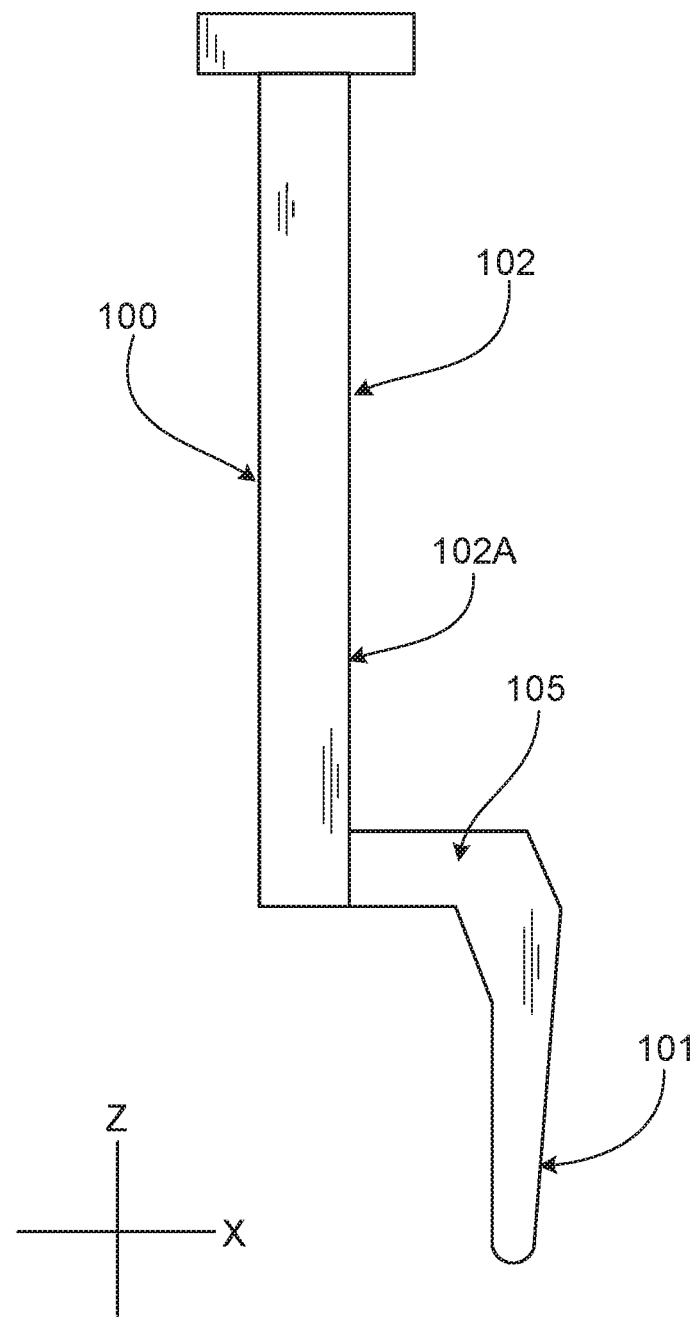
FIG. 2 is a schematic front view of an improved femoral broach.
Figure 3:
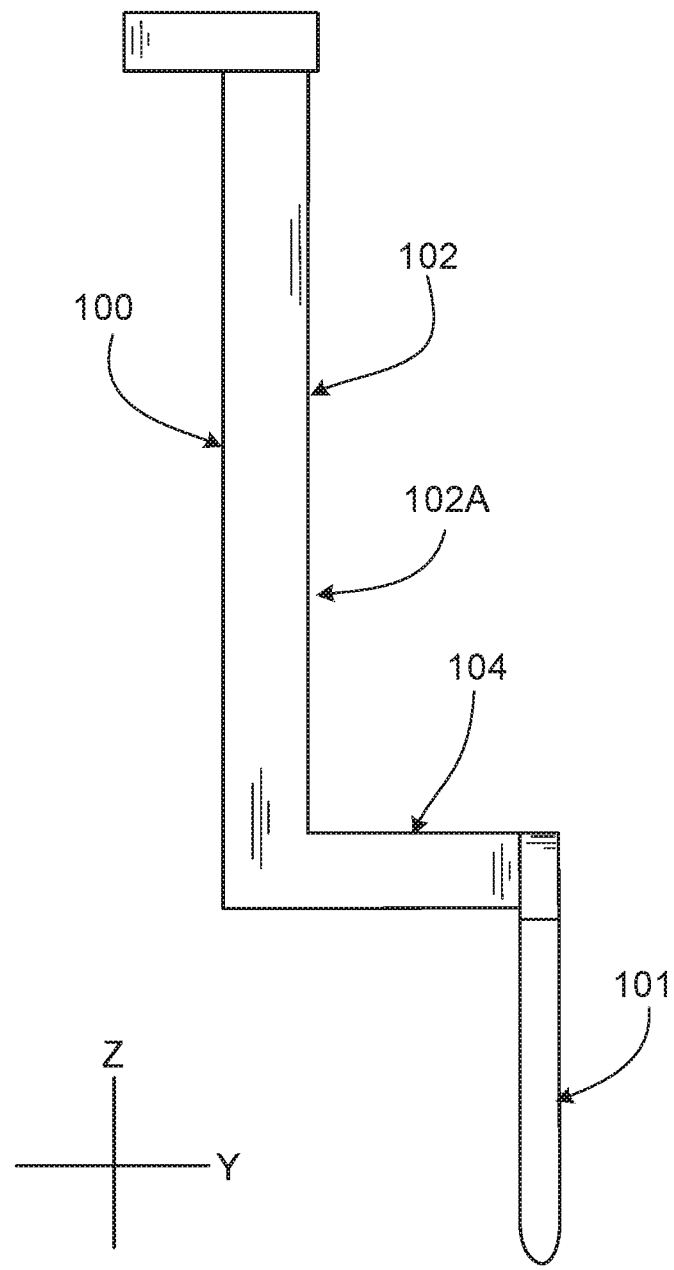
FIG. 3 is a schematic side view of an improved femoral broach.
Figure 4:
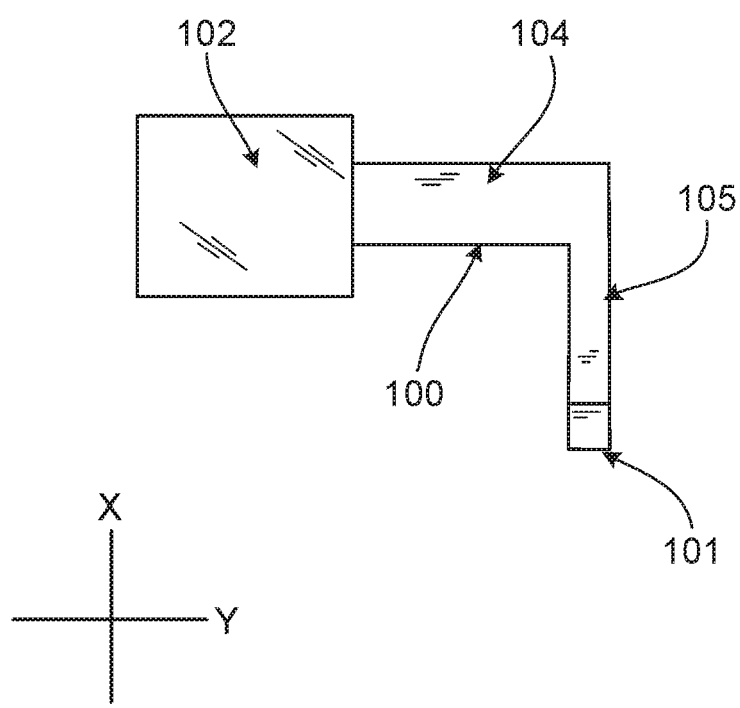
FIG. 4 is a schematic top view of an improved femoral broach.
Figure 5:
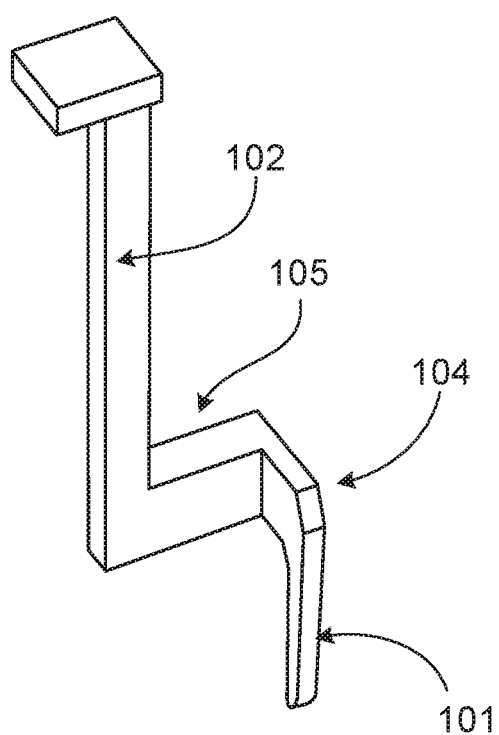
FIG. 5 shows a schematic model of an improved femoral broach.
Figure 6:
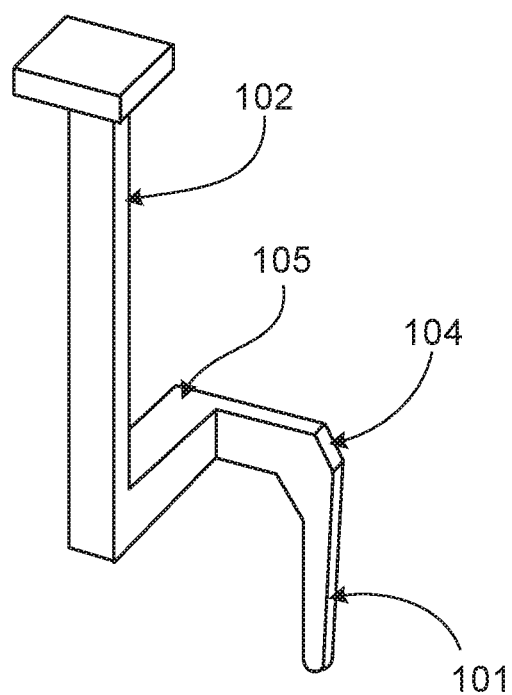
FIG. 6 shows a schematic model of an improved femoral broach.
Figure 7:
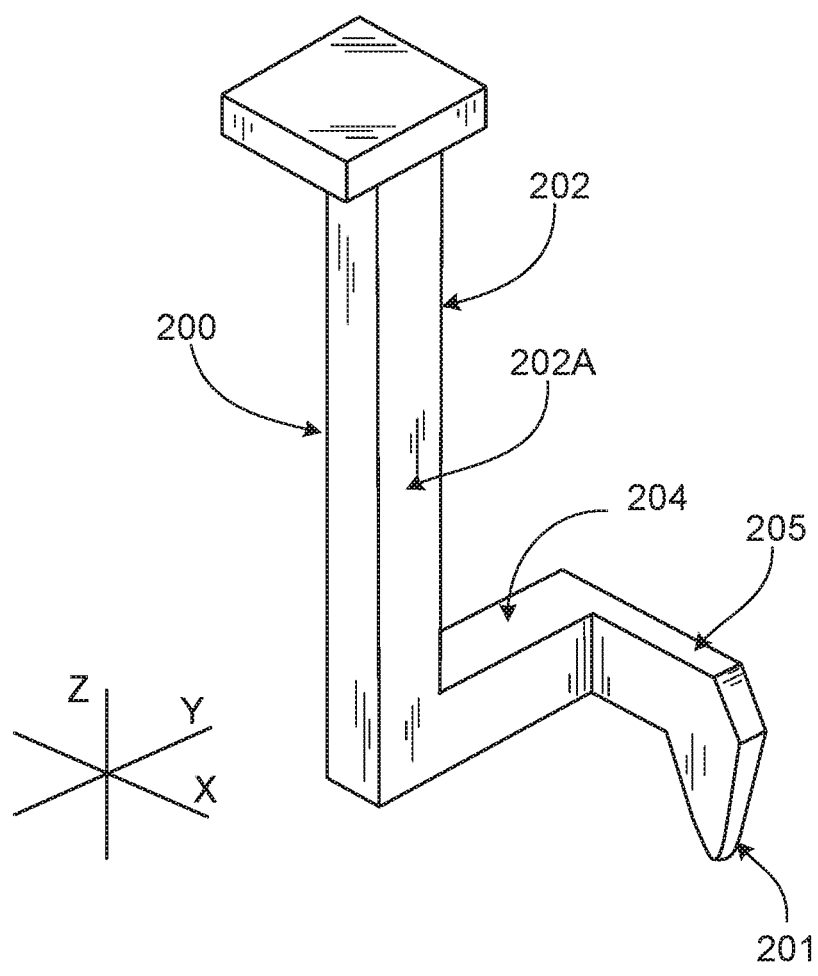
FIG. 7 is a schematic isometric view of an improved femoral osteotome.
Figure 8:
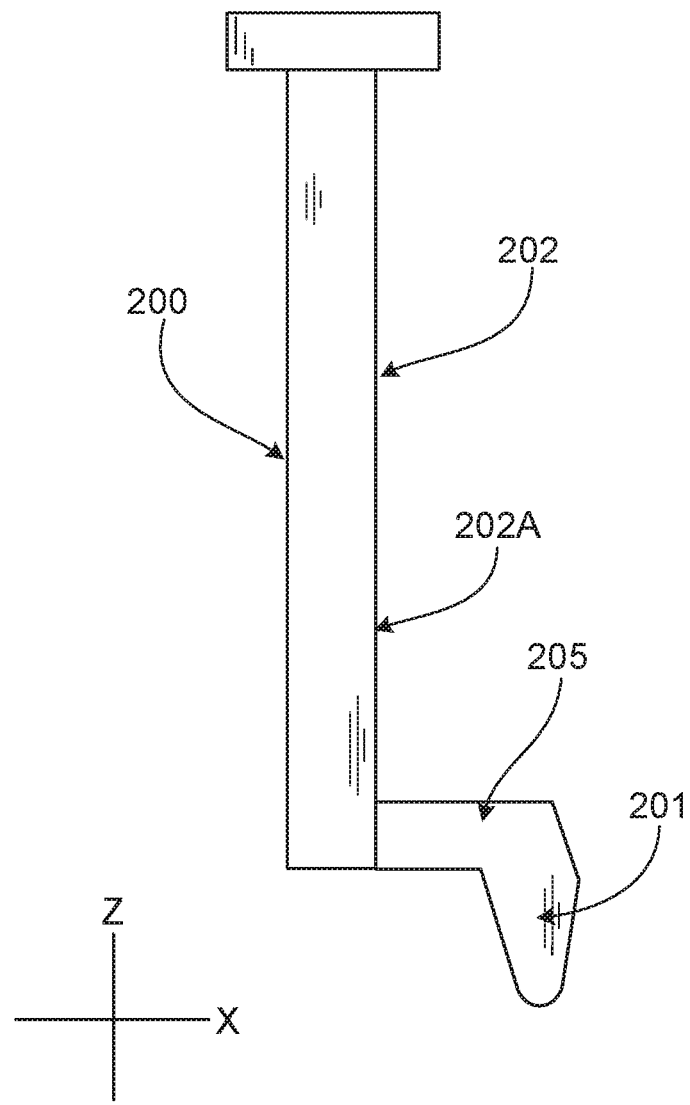
FIG. 8 is a schematic front view of an improved femoral osteotome.
Figure 9:
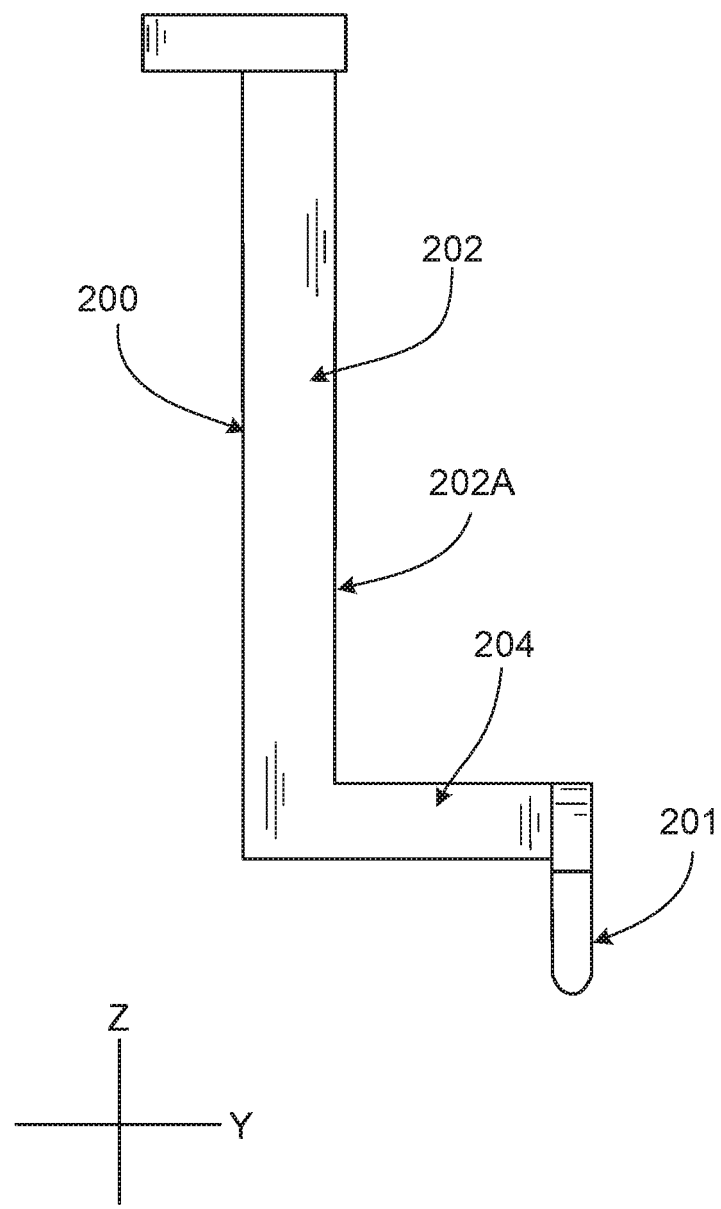
FIG. 9 is a schematic side view of an improved femoral osteotome.
Figure 10:
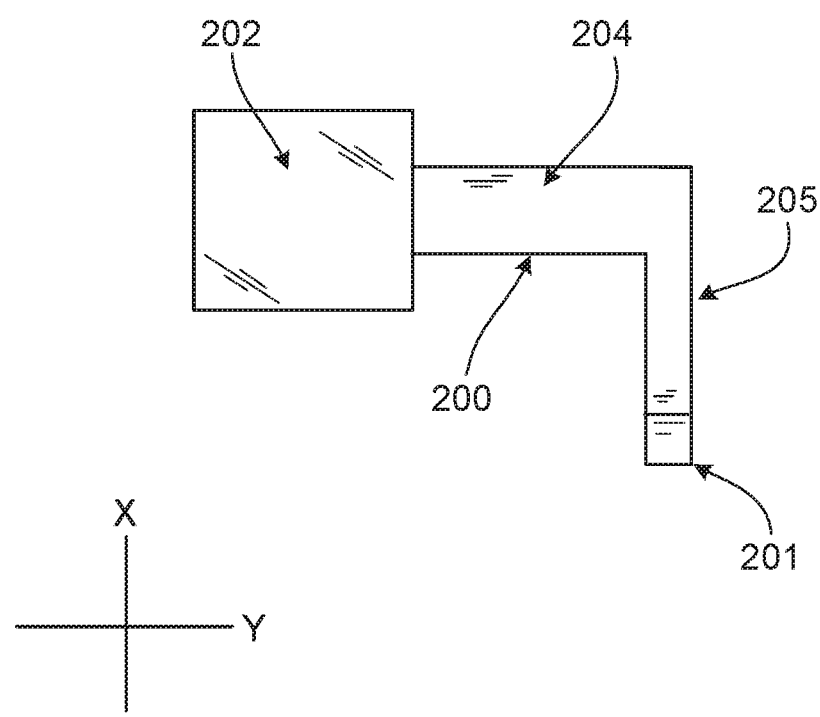
FIG. 10 is a schematic top view of an improved femoral osteotome.
Figure 11:
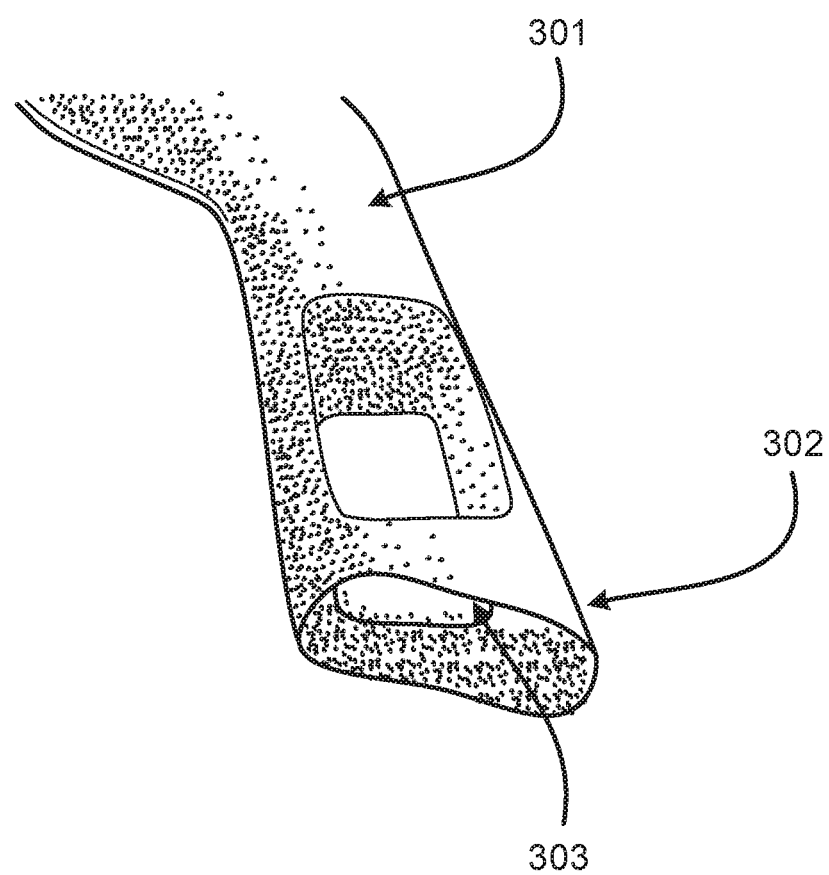
FIG. 11 is an isometric view of a cutting element of a box osteotome.

FIGS. 1-6 show an improved femoral broach (100). For ease of description the devices disclosed herein will be described with respect to Cartesian coordinates, in which the x- and y-axes lie in a horizontal plane, and the z-axis extends vertically. However, it will be appreciated that this method of description is for convenience only and is not intended to limit the invention to any particular orientation. Likewise, unless otherwise stated, terms used herein such as "top," "bottom," "upper," "lower," "left," "right," "front," "back," "proximal," "distal," "medial," "lateral," "inferior," "superior," "anterior," "posterior" and the like are used only for convenience of description and are not intended to limit the invention to any particular orientation.

The improved femoral broach (100) comprises a handle (102) an elongated shaft (102A) extending downward from the knob approximately in the z-direction. At the bottom of the handle shaft (102A), a first offset (104) extends transversely approximately in the y-direction. At the other end of the first offset (104), a second offset (105) extends transversely approximately in the x-direction. At the other end of the second offset (105), a shaping member (101) is elongated downward approximately in the z-direction and is adapted for insertion into the femoral cavity.

The double offset of the handle member (102) with respect to the shaping member (101) simplifies the approach to the femur, and permits inserting and operating the broach through a minimally invasive surgical incision, reducing the need for the posterior capsule resection during anterior approach to the femur. In a preferred embodiment, this configuration allows the surgeon to advantageously utilize the anterior approach over more invasive lateral or posterior approaches. The double offset of the handle (102) with respect to the shaping member (101) permits aligning the shaping member (101) with the long axis of the femur, at the same time directing the handle up and out of the surgical site, rendering vertical approach to the femur unnecessary.

During surgery, the first offset (104) elevates the handle (102) out of the wound during and upon insertion of the broach. When the patient is in a supine position, during and upon insertion of the broach, the handle (102) of the broach is elevated in a generally vertical direction. The second offset (104) minimizes the trauma to the bone and to the soft tissues. When the patient is in a supine position, the second offset (104) locates the handle away from the shaping member in the general medial/lateral direction The broaches according to the embodiment shown in FIGS. 1-6 can be advantageously inserted through a minimally invasive surgical incision and are particularly advantageous for anterior access to the femur that is preferred to the lateral or posterior access that requires significant muscle dissection, increasing the surgical time and the time required for the patient to return to normal daily activities. In a preferred embodiment, the incision for inserting the improved femoral broach is between approximately 4 to approximately 16 cm. The broaches according to the embodiment shown in FIGS. 1-6 can be advantageously utilized with a variety of hip prostheses, such as, but not limited to, those employing the Mueller femoral stem. In a preferred embodiment, the broaches according to the embodiment shown in FIGS. 1-6 allow the surgeon to utilize a less invasive anterior approach without posterior capsule release in order to install a femoral member of the hip prosthesis.

When preparing the femoral cavity for installation of the prosthetic hip femoral component, the surgeon inserts into and may rotate along the medial arc of the femoral intramedullary canal or cavity a series of the broaches of increasing size, thereby expanding the internal cavity of the femur until a desired shape is created. According to aspects and embodiments of the present invention, to minimize trauma to a patient during installation and operation of the improved broaches, the surgeon changes the angle of insertion of the broach, utilizing the double offset of the handle to align the elongated member of the broach with the long axis of the femur when approaching the femur through an anterior incision at the patient's hip.

To improve the alignment of the broach during insertion into the femur, various alignment systems and methods may be utilized, including, but not limited to, mechanical referencing, alignment, and positioning devices. Computer-assisted or computer-aided surgery systems can also be advantageously used in conjunction with the improved broaches of the embodiments of the present invention. For example, the broaches can be used with the sensors that track the instruments with respect to the patient's femur, and a computer functionality processing information provided by the sensors and providing recommendations to the surgeon. The improved broaches can further comprise fiducials for tracking the instrument during computer-assisted surgery.

Robotic navigation devices and surgical systems can also be used to navigate and operate the improved broaches.

The improved broaches and method of their use according to aspects and embodiments of the present invention possess a number of advantages over the conventional systems and methods. Some of the conventional methods and devices for femoral preparation are designed with the goal of minimizing the amount of bone resected from the greater trochanter to gain access to the intramedullary cavity of the femur. To this end, the conventional systems employ the femoral broaches that are rotated along the medial arc of the patient's femur when preparing the femoral cavity. A surgeon uses a series of the increasing size broaches until an appropriate femoral cavity is created. In such conventional systems, the broach handle is offset medially with respect to the part of the broach inserted into the femur. In contrast to the conventional systems, the broach systems according to aspects and embodiments of the present invention are advantageously adapted for use with the anterior approach by incorporating a second, vertical, offset of the handle with respect to the part of the broach inserted into the femur during its operation.

According to aspects and embodiments of the present invention, variations are envisioned on the improved devices and systems used for creating a femoral cavity during hip arthroplasty. The improved broaches of the present invention can be of variable shape, thereby allowing changing their configuration to suit a particular surgical application. The broaches of variable shape can incorporate, for example, flexible shafts that permit altering their shape. The broaches of variable shape can also be modular, thereby allowing the user to custom-assemble a broach for a particular application. Also envisioned are flexible reamers for opening, or reaming, a femoral canal, and flexible milling systems for rotating into the femur. All of the embodiments provided herein can be used separately or in any combination.

Osteotome

FIGS. 7-11 show an improved femoral osteotome (200). The improved femoral osteotome (200) comprises a handle (202) an elongated shaft (202A) extending downward from the knob approximately in the z-direction. At the bottom of the handle shaft (202A), a first offset (204) extends approximately in the y-direction. At the other end of the first offset (204), a second offset (205) extends approximately in the x-direction. At the other end of the second offset (205), a shaping member (201) is elongated downward approximately in the z-direction and is adapted for insertion into the femoral bone.

The double offset of the handle member (202) with respect to the shaping member (201) simplifies the approach to the femur, and permits inserting and operating the osteotome through a minimally invasive surgical incision, reducing the need for the posterior capsule resection during anterior approach to the femur. In a preferred embodiment, this configuration allows the surgeon to advantageously utilize the anterior approach over more invasive lateral or posterior approaches. The double offset of the handle (202) with respect to the shaping member (201) permits aligning the shaping member (201) with the long axis of the femur, at the same time directing the handle up and out of the surgical site, rendering vertical approach to the femur unnecessary.

During surgery, the first offset (204) elevates the handle (202) out of the wound during and upon insertion of the osteotome. When the patient is in a supine position, upon insertion, the handle (202) of the osteotome is elevated in a generally vertical direction. The second offset (204) minimizes the trauma to the bone and to the soft tissues. When the patient is positioned in a supine position on a surgical table, the second offset (204) locates the handle (202) away from the long the shaping member (201) in the general medial/lateral direction In a preferred embodiment, the osteotome is a box osteotome comprising a shaping member (301) shown in FIG. 11. The shaping member (301) of the box osteotome is of approximately box shape and comprises an open distal end (302) with a distal cutting edge (303). During hip arthroplasty, the box osteotome cuts a box shape of the femoral bone to open the patient's femoral canal. In a preferred embodiment, the cutting member (301) of the box osteotome is approximately 1 to 1½ inches long.

The osteotomes according to the embodiment shown in FIGS. 7-11 can be advantageously inserted through a minimally invasive surgical incision and are particularly convenient for the anterior access to the femur, which is advantageous over the lateral or posterior access requiring the surgical dissection of muscle tissue. In a preferred embodiment, the incision for inserting the improved osteotome is between approximately 4 cm to approximately 16 cm.

In one embodiment, the improved osteotomes are advantageously, but not necessarily, utilized in conjunction with the improved broaches. More specifically, the osteotome is used to remove the trochanteric fossa. When preparing the femur for installation of the prosthetic hip femoral component, the surgeon uses the osteotome to resect at least a part of the femoral greater trochanter in order to gain access to the central portion of the femur. According to aspects and embodiments of the present invention, to minimize trauma to the patient during operation of the improved osteotome, the surgeon changes the angle of insertion of the osteotome, utilizing the double offset of the handle to appropriately direct the elongated cutting member of the osteotome in the greater trochanter resection.

To improve the alignment of the osteotome during insertion into the femur, various alignment systems and methods may be utilized. Such systems may include mechanical referencing, alignment, and positioning devices. Computer-assisted or computer-aided surgery systems can also be advantageously used in conjunction with the improved osteotomes of the embodiments of the present invention. For example, the osteotomes can be used with the sensors' tracking instruments with respect to the patient's femur and a computer functionality that processes the information provided by the sensors and, in turn, provides navigational recommendations to the surgeon. The improved osteotomes can further comprise fiducials for tracking the instrument during computer-assisted surgery. Robotic navigation devices and surgical systems can also be used to navigate and operate the improved osteotomes.

System and Method for Improved Positioning of a Patient

The aspects and embodiments of the present invention provide a method and system for improving patient positioning during hip arthroplasty. The improved method allows the surgeon better access to the hip joint, particularly to the femur. The improved method also and permits quick and simple modification of the conventional surgical tables to improve patient positioning during hip arthroplasty.

Figure 12:
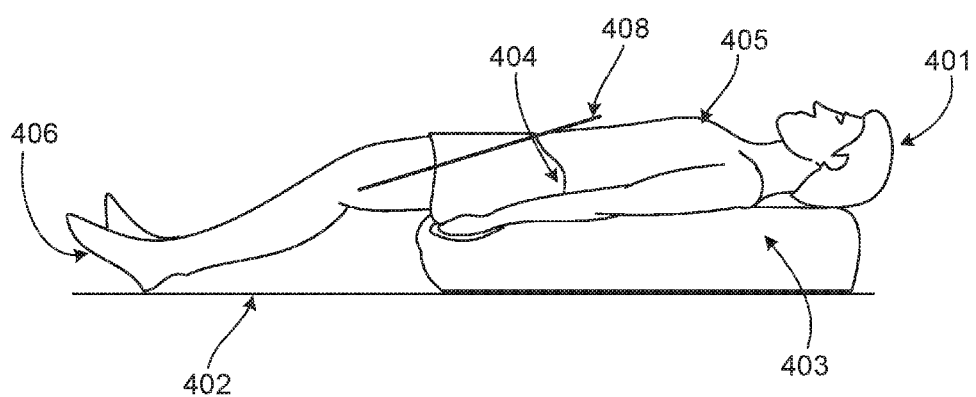
FIG. 12 is a schematic representation of a method of improved patient positioning during hip arthroplasty.

According to an embodiment of the present invention schematically illustrated in FIG. 12, for hip replacement surgery, the patient (401) is placed on a surgical table (402) fitted with a mattress of variable configuration (403), such as, but not limited to, an air mattress or an inflatable mattress. When improved access to the proximal femur (404) is desired during the surgery, the configuration of the mattress (403) is altered to elevate the patient's torso (405) with respect to the patient's leg (406). To this end, the mattress of variable configuration (403) may be placed under the patient's torso (405) with the leg (406) positioned on the surgical table (402). Increasing the height of the mattress (403) elevates the patient's torso (405) relative to the patient's leg. The torso's (405) elevation directs the proximal end of the femur (404) towards the surgical incision (the general direction of the long femoral axis is also indicated (408)). In one aspect, this provides the surgeon enhanced access to the femur for preparation of the intramedullary canal for total hip arthroplasty, without resecting the posterior capsule.

Thus, by using the variable configuration mattress to elevate the torso of the patient relative to the patient's leg, the leg of the patient becomes positioned at an angle relative to the torso, thereby allowing easier access to the proximal femur at the hip joint. The concept of using the variable configuration mattress for positioning of the patient and the patient's body parts during surgery is not limited to hip arthroplasty, but can be adapted to other surgical procedures.

In a preferred embodiment, using the variable configuration mattress during hip arthroplasty allows repositioning of the patient's leg throughout surgery to gain better access to the femur for installation of the femoral component of the prosthetic hip. With the variable configuration mattress, any operating room table can be adapted for such a procedure, thereby avoiding the necessity of fitting the surgical suite with a table with a dropping end, such as a Judet table. Using the variable configuration mattress increases the versatility of a surgical suite without incurring the significant cost of purchasing an additional surgical table.

In a preferred embodiment, the variable configuration mattress according to aspects and embodiments of the present invention is an inflatable mattress. An inflatable mattress is manufactured according to methods known to those of ordinary skill in the art. The variable configuration mattress can be sectional, allowing the user to alter the configuration of the mattress' sections in any desired combination. In this variation, for example, the configuration of the section of the mattress fitted under the patient's torso may be altered to elevate the torso, or the configuration of the section of the mattress fitted under the patient's leg may be altered to lower the limb, or both. The variable configuration mattress can incorporate side sections to prevent the patient from rolling off the mattress. When an inflatable mattress is used, it is inflated to increase the height of the mattress or one or more of its sections, and deflated to decrease the height of the mattress or one or more of its sections. The air mattress can be disposable or reusable depending on the materials used and the methods of construction. The variable configuration of the inflatable mattress, including but not limited to the change of height of the mattress or its sections, can be utilized for positioning together with other devices, such as, but not limited to, sand bags or rigid pads.

Variations on the devices, instruments, systems, and methods according to preferred embodiments of the present invention are envisioned and fall within the scope of the present invention. In general, it is to be understood that the structures and methods according to aspects and embodiments of the present invention can vary, and can be modified in accordance with a particular application for which they are used. Incorporation of various useful features by the structures and methods and their use in conjunction with various devices and systems is envisioned and falls within the scope of the present invention. It is also to be understood that advantageous and distinguishing features according to embodiments of the present invention can be present in various combinations.

In one of its aspects, the present invention also provides methods of modifying a shape of a proximal femur, including removing femoral bone or other tissues, or modifying the shape of the femoral bone or other tissues, using the instruments, systems, and methods according to embodiments of the present invention. Specifically, the present invention provides a method of preparing a femur of a patient for installation of a stem of a femoral component of a prosthetic hip during hip replacement surgery. Shaping the proximal femur using the instruments such as the osteotomes and the broaches, comprises inserting the instrument into the hip joint, positioning the instrument, shaping the tissue with the instrument, and removing the instrument from the hip joint.

According to other aspects, the instruments, devices and systems, such as broaches and osteotomes, are used to conduct joint replacement surgery, such as hip replacement surgery. Such processes can include any or all of inserting the instrument into a hip joint, positioning the instrument, shaping the tissue with the instrument, removing the instrument from the site, inserting a femoral prosthetic component, and completing the surgery.

The particular embodiments of the invention have been described for clarity, but are not limiting of the present invention. Those of skill in the art can readily determine that additional embodiments and features of the invention are within the scope of the appended claims and equivalents thereto.

What is claimed:

1. A device for preparing a femoral canal of a patient during surgery comprising:
a handle comprising a distal portion, a transition portion, and a proximal portion;
wherein said distal portion is adapted to attach to an implement;
wherein said proximal portion of the handle has a first longitudinal axis;
wherein the implement has a second longitudinal axis;
wherein said transition portion extends from the distal portion of the handle to the proximal portion of the handle so that the first longitudinal axis of the proximal portion of the handle is substantially parallel to the second longitudinal axis of the implement, and the transition portion is angled relative to the first longitudinal axis of the proximal portion in both a posterior direction and a medial-lateral direction;
wherein the handle comprises a dual offset including a bend in the anterior-posterior direction and a bend in the medial-lateral direction; and
wherein the implement has a non-circular cross section with a major dimension and a perpendicular minor dimension, the major and minor dimensions extending perpendicular to the second longitudinal axis, wherein no plane through the implement containing the major dimension and the second longitudinal axis is coplanar with a single plane through the proximal portion and the distal portion containing both first and second longitudinal axes.

2. The device of claim 1, wherein the implement is a shaping instrument.

3. The device of claim 2, wherein the proximal portion of the shaping instrument is removably affixed to said distal portion of the handle.

4. The device of claim 2, wherein the shaping instrument is a rasp.

5. The device of claim 1 further comprising an impaction face affixed to said proximal portion of the handle.

6. The device of claim 1, wherein said handle is adapted for use with an automatic impaction device.

7. The device of claim 1, wherein the transition portion extends from a proximal end of the distal portion of the handle to a distal end of the proximal portion of the handle.

8. The device of claim 1, wherein the handle and the implement are separate detachable pieces.

9. The device of claim 1, wherein the bend in the anterior-posterior direction has substantially the same bend as the bend in the medial-lateral direction.

10. The device of claim 9, wherein the bend in the anterior-posterior direction has substantially the same bend as the bend in the medial-lateral direction.

11. The device of claim 9, further comprising an impaction surface on the proximal portion.

12. The device of claim 9, wherein the transition portion extends from a proximal end of the distal portion of the handle to a distal end of the proximal portion of the handle.

13. The device of claim 9, wherein the handle and the implement are separate detachable pieces.

14. A device for preparing a femoral canal of a patient during surgery comprising:
   a handle comprising a distal portion, a transition portion, and a proximal portion;
      wherein said distal portion is adapted to attach to an implement;
      wherein said proximal portion has a first longitudinal axis;
      wherein said implement has a second longitudinal axis;
      wherein said transition portion extends from the distal portion to the proximal portion so that the first longitudinal axis of the proximal portion is substantially parallel to the second longitudinal axis of the implement, and so that the transition portion is angled relative to the first longitudinal axis of the proximal portion both in a posterior direction and a lateral direction; wherein the device comprises a dual offset including a first bend between the transition portion and the proximal portion and a second bend between the transition portion and the distal portion, wherein the bends include both a bend in the anterior-posterior direction and a bend in the medial-lateral direction; and
   wherein the implement has a non-circular cross section with a major dimension and a perpendicular minor dimension, the major and minor dimensions extending perpendicular to the second longitudinal axis, wherein no plane through the implement containing the major dimension and the second longitudinal axis is coplanar with a single plane through the proximal portion and the distal portion containing both first and second longitudinal axes.

15. A device for preparing a femoral canal of a patient during surgery comprising:
   a proximal portion having a first longitudinal axis;
   a transition portion; and
   a distal portion adapted to attach to an implement, the distal portion having a second longitudinal axis;
   wherein said transition portion extends from the distal portion of the device to the proximal portion of the device so that the transition portion is angled relative to the first longitudinal axis of the proximal portion in a posterior direction and a medial-lateral direction;
   wherein the device comprises a dual offset including a bend in the anterior-posterior direction and a bend in the medial-lateral direction; and
   wherein no plane extending through the proximal portion is coplanar with a plane extending through both the transition portion and the distal portion.

* * * * *